United States Patent [19]

Frenkel et al.

[11] 4,391,822

[45] Jul. 5, 1983

[54] METHOD FOR PREVENTING CATS FROM SHEDDING TOXOPLASMA OOCYSTS AFTER INFECTION OF SUCH CATS

[75] Inventors: Jacob K. Frenkel, Overland Park, Kans.; Donald D. Smith, Independence, Mo.

[73] Assignee: Kansas University Endowment Association, Lawrence, Kans.

[21] Appl. No.: 403,788

[22] Filed: Jul. 30, 1982

[51] Int. Cl.³ .............................................. A61K 31/35
[52] U.S. Cl. .................................................... 424/283
[58] Field of Search ....................................... 424/283

[56] References Cited
PUBLICATIONS

Dubey et al., Chem. Abst., vol. 87, (1977), p. 95742b.

Primary Examiner—Sam Rosen
Attorney, Agent, or Firm—Schmidt, Johnson, Hovey & Williams

[57] ABSTRACT

A method of preventing, or at least substantially minimizing, shedding of Toxoplasma oocysts by cats is described which can be begun after infection of the cat and may serve to reduce the contamination with infectious oocysts of soils around areas of human habitation. The method involves administration, in effective amounts of a drug agent selected from the group consisting of monensin or salinomycin. The administration is preferably oral, and can be accomplished by mixing the drug with the cat's food or via a slow release dosage form. The drug treatment is normally commenced within about two days after infection, and is continued for a period of at least about two weeks.

9 Claims, No Drawings

METHOD FOR PREVENTING CATS FROM SHEDDING TOXOPLASMA OOCYSTS AFTER INFECTION OF SUCH CATS

BACKGROUND OF THE INVENTION

1. Field of the Invention

The present invention is broadly concerned with a method of preventing or minimizing shedding of Toxoplasma oocysts by cats in their fecal elimination processes and thereby reducing the contamination of soils around human habitations. More particularly, it is concerned with such a method which can be begun after the cat has been subjected to infection, i.e., after the cat has eaten meat (e.g., a wild bird or mouse) which carries Toxoplasma cysts or related forms.

2. Description of the Prior Art

Cats and people are biologically close enough for them to be able to suffer from some of the same diseases and parasites. Some of these ailments are well known—rabies, because it is so dramatic and terrible, and fleas, because they are so common, are two familiar examples. Less familiar is Toxoplasmosis, an animal disease that can be transmitted to man. It is common to all domestic animals, including barnyard species, and, when present, travels through cat feces and through meat.

Any direct contact with cat feces or fecally contaminated soil increases the likelihood of contagion. Cattle and sheep can become infected by ingesting contaminated soil while grazing. Birds may become infected when eating seeds on the ground or from eating contaminated earthworms. However, a domestic cat, after stalking a mouse or bird, may become a disseminator of the disease. Although infected animals may be means of transmitting disease, more often than not there is no sign of illness.

Toxoplasmosis is a parasitic disease, and research has indicated that the parasite has a complicated life cycle which spreads the disease through many animals. Oocysts (egg spores) are shed in the feces of domestic cats and certain types of wild cats. Oocysts are then deposited in soil where they persist for many months. Flies and cokroaches, which eat feces, can serve as transport agents, contaminating animals which do not directly encounter the cat feces or contaminated soil. Mice and birds can be infected either from transport agents or through direct contact or contaminated soil and can then spread the infection to animals which prey on them. Humans can be infected by eating raw or rare meats, or by direct contact with infected cat feces or contaminated soil.

Toxoplasma infections are quite prevalent, with one-quarter to one-half of the adults in the United States and elsewhere asymptomatically infected. While the presence of Toxoplasma infections has long been known, little was discovered about the transmission of Toxoplasma until the late 1930's and 1940's when Toxoplasma was found in newborn babies in the U.S. However, the life cycle of toxoplasma, and the central role played therein by cats, has now been conclusively established.

The spectrum of human disease due to Toxoplasma was characterized by a combination of serologic, immunologic and epidemiological studies, and by isolation of Toxoplasma. In the acute infection where cells are destroyed by rapidly proliferating organisms, there may occur fever, pneumonia, an inflammation in the heart muscle, liver and skin (rash). Toward the end of this period or following a subclinical acute infection, localized or generalized swelling of lymph nodes is observed, especially in women. In newborns infected in utero, a subacute disease picture is typical. In addition to the symptoms of acute Toxoplasmosis mentioned above, meningoencephalitis ("brain fever"), often with hydrocephalus ("water on the brain"), and retinochoroiditis (intraocular inflammation) are important. Most of the mothers who have given birth to infected babies had asymptomatic infections.

Thus, Toxoplasmosis deserves special attention because of the serious danger it raises for the unborn human baby. A pregnant woman may contract the infection and unknowingly infect the fetus. Even if diagnosed and treated, her child may nevertheless be born with permanent brain and eye damage. Surveillance of pregnant women for diagnosis and eventual treatment would be a difficult and costly process. For this reason, efforts to prevent infection during pregnancy are most important.

Inasmuch as cats shed Toxoplasma oocysts after a prepatent (incubation) period of three to ten days after ingestion of cysts in infected animal tissues, it is especially important that such oocyst shedding be controlled or preferably eliminated. That is to say, a normal domestic house cat, while being fed a standard cat food or other ration, may, at infrequent intervals, hunt and eat raw meat such as wild birds and mice, and thereby become infected. The problem, of course, is that it is very difficult to completely control a cat's diet, particularly in cases where the cat has substantial outdoor freedom. A further complication noted above is the fact that primary Toxoplasma infection of cats, during which infectious oocysts are shed, is usually inapparent. Consequently, the soil of yards and gardens close to human habitation can be contaminated with oocysts without raising the suspicion of even an observant cat owner. Such infectious oocysts tend to remain active for a period of months up to a year and a half, thereby presenting a significant health hazard for pregnant women and young children.

Prior attempts to control oocyst shedding were not highly satisfactory. Attempts have been made to administer sulfadiazine alone or with pyrimethamine to cats starting five days after the infectious meal, thereby reducing the number of shed oocysts but not preventing shedding. Pyrimethamine and sulfadiazine have been administered by intramuscular injection; however, when given by mouth these compounds were less effective. Also, the potential toxicity of these drugs suggested the need for blood counts or the administration of antagonists, which is both expensive and time consuming. Other workers have administered a sulfone, sulfadiazine, pyrimethamine, and Clindamycin to cats between two days before to three to four days after infection with Toxoplasma; this served to diminish the shedding in the case of some cats, but did not consistently eliminate this objectionable result.

A number of polyether ionophores are active against coccidia of Eimeria species in chicken and cattle, such as lasalocid, monensin, and salinomycin. However, prior workers administering lasalocid at 5–10 mg./kg./day in two divided doses, mixed with canned cat food, starting the day before infection and continuing for fourteen days, prevented oocyst shedding in only three of nine cats. In short, while the objective of preventing oocyst shedding in infected cats has been studied by others, there is a decided need in the art for a method of preventing such shedding, particularly in the case of domestic cats that obtain a substantial part of their food at home, but that hunt when they escape or are let out of the house.

SUMMARY OF THE INVENTION

The present invention overcomes the problems outlined above and provides a greatly improved method for, in many cases, completely eliminating the phenomenon of oocyst shedding by Toxoplasma-infected cats. Broadly speaking, the method of the invention involves administering to an infected cat, prior to the onset of oocyst shedding, an effective amount of an agent selected from the group consisting of monensin and salinomycin, and continuing such administration for a period of time thereafter.

Monensin is the most preferred drug in accordance with the invention, and is generally administered at a level of at least about 200 mg. per kg. of cat ration, advantageously on a daily basis. The most preferred level of administration is from about 200 to 300 mg. per kg. of cat ration per day. On the other hand, in the case of salinomycine, the level of administration should be at least about 50 mg., per kg. of cat ration per day, and more preferably from about 50 to 100 mg. per kg. of cat ration per day. In both cases, the drug can be simply admixed with normal cat food, and for convenience prepared as a mixture, or the drug can be given as a tablet, capsule or time release preparation. To be effective, the administration of the drug should commence within about one to two days from the time of ingestion by the cat of Toxoplasma-infected food, and should continue for a period of at least about two weeks thereafter.

Although administration of monensin or salinomycin through use of a prepared ration containing the drug in proper amounts is preferred for reasons of ease of administration, other methods are possible so long as the drug is maintained in the intestine of the animal. For example, the medication could also be administered in a time-release dosage form such as a tablet or capsule. In this event, monensin should be administered at a level of from about 6 to 8 mg. per kg. of body weight of the cat per day during the period of time drug treatment is effective for prevention of oocyst shedding. Salinomycin should be used at a level of about 2 to 3 mg. per kg. of cat body weight.

A particular advantage of the invention is the fact that cats can be treated on a "morning after" basis. That is to say, it is not necessary that the monensin or salinomycin be administered prophylactically, but can be given to the cat with its food even after the cat has returned from the outside and has potentially become infected with Toxoplasma. Thus, cats who are normally held indoors but who occasionally escape or are let outside for short periods of time, need only be treated after their return in the manner outlined above.

DESCRIPTION OF THE PREFERRED EMBODIMENT

The preferred methods in accordance with the present invention, are set forth in the following example. It should be understood in this respect, however, that the example is provided for purposes of illustration only, and should not be taken in a limiting sense.

EXAMPLE

Materials and Methods

Kittens used in this example were raised in the laboratory or obtained as weanlings from private donors. They weighted between 610 and 1745 gms (means $1162 + 348$ gm) and were between two and five months old. Female CF1 strain mice weighing about 25 gm. each were obtained from Mid-Continent Research, Inc., Shawnee, Kans. 66202; Crystalline monensin sodium (lots X-34933 and X-31357; potency 899 mg/g) was obtained from Elanco Products, Division of Eli Lilly and Co., Indianapolis, Ind. 46206. The drug was mixed at concentrations of 100 or 200 mg/kg (0.01–0.02%; 100–200 ppm) in ground Purina Cat Chow (30% protein) for most cats and in Purina Kitten Chow (35% protein) for newly weaned kittens, and was administered ad libitum. Between 25 and 40 gm food was consumed daily by kittens weighing approximately 1 kg., or 3–4 or 6–8 mg. of monensin per kitten per day.

Six experiments were performed with four to six kittens in each, using either 0.01 or 0.02% monensin (total 19) with one to four untreated control kittens (total 10). The drug was usually started before infection unless otherwise indicated and continued for 8 to 19 days (Table 1). The effects of monensin on parts of the enteric cycle of Toxoplasma were studied in two experiments (Table 2). Fecal specimens were examined at daily or alternate day intervals for 28–30 days. After one month, the kittens were challenged per os with the identical strain of Toxoplasma, and after two to three months, most were challenged with a heterologous isolate. The feces were examined for the appearance of oocysts after each inoculation. The body weights, serum chemistry and certain hematologic values were determined at intervals for 7 weeks in 4 uninfected monensin-treated and 4 control kittens that had just been weaned. The treated kittens were killed and their tissues examined histologically.

Infectious inocula for kittens consisted of triturated brain tissue and carcasses of mice chronically infected with cysts of *T. gondii*. Strains M-7741 isolated from a sheep in the United States, and for challenges, strain Gail originally isolated from a human patient in Germany, were maintained as chronic infections in mice. A number of mouse brains equivalent to the number of cats per experiment were combined and homogenized, and equal doses were placed into the posterior pharynx of each experimental cat; thereafter each cat was fed a portion of each mouse carcass.

Feces were collected from kittens daily for 30 days after the initial exposure to Toxoplasma and three times weekly after challenge. Any oocysts present were concentrated by flotation in a sucrose solution of specific gravity 1.15 and stored in 2% (v/v) sulfuric acid to permit sporulation (Frenkel, "Toxoplasmosis", *Current Veterinary Therapy*, R. W. Kirk (ed.) W. B. Saunders Co., Philadelphia, Pa. 5:775–780, 6:1318–1324 (1974)) Shedding intensity was graded on a scale of 1–4; (1+ =one oocyst per slide, 2+ =many oocysts per slide, 3+ =one oocysts per high dry field, and 4+ =many oocysts per high dry field). In some experiments counts of oocysts were made by standard techniques using a hemacytometer. In order to determine whether samples taken after primary and challenge infections and judged negative by flotation were really free of oocysts, they were fed to mice. Fecal samples from individual kittens were neutralized with 3.3% (w/v) sodium hydroxide, using phenol red as indicator, and fed to groups of two mice each. To avoid mortality these mice were treated with sodium sulfadiazine, 30 mg/100 ml in the drinking water and tested for Toxoplasma serologically after 20 days.

Mice were bled from the retro-orbital sinus while under ether anesthesia, and cats were bled from the ear. Antibody titers were determined by Sabin-Feldman's dye test (Frenkel and Jacobs, "Ocular Toxoplasmosis", A.M.A. Arch. Ophth. (Chicago) 59:260-279 (1958)), utilizing tachyzoites of the RH strain of Toxoplasma maintained in acutely infected mice and passed twice weekly intraperitoneally. Antibody titers were determined on the cats before each infection or challenge. None of the cats had antibody at 1:2 final serum dilution prior to infection.

Results

Monensin in food at 0.02% prevented shedding of oocysts in all of nine kittens, whereas, at 0.01% three out of four kittens shed oocysts. All 10 control kittens shed oocysts (Table 1). One kitten from the control group died after 8 days with Toxoplasmosis. When challenged orally after one month, 7/9, 4/4 and 8/9 kittens respectively, were immune as shown by nonshedding of oocysts. Each challenge inoculum was shown infectious by feeding it to untreated, nonimmune control cats, all of which shed oocysts. Oocyst shedding was completely suppressed when monensin was given starting −2 to +1 days after infection and continued for from 6 to 15 days. Suppression was seen in only one of seven cats receiving drug beginning day +2 or later, and continuing from 4 to 18 days. When the drug was delayed until the third day, there was no effect on oocyst shedding.

Prior to use all 29 cats were devoid of toxoplasma antibody in the dye test using a 1:2 final dilution. Antibody titers after 28-62 days reached 1:64 to 4000; however four kittens had an undetectable titer.

Oocysts of Cystoisospora felis only were seen in six kittens, and C. felis and C. rivolta in three kittens, and in 26 kittens no Cystoisospora was seen. No effect of monensin was noted on these established Cystoisospora infections; similarly to the lack of effect on established toxoplasma infections (Table 2).

Fecal samples of all cats, which were judged negative microscopically, after primary infection and after challenge, were inoculated into mice after allowing time for any oocysts present to sporulate, usually combining several and up to seven fecal specimens. In all 22 samples the mice remained sero-negative.

Body weights of 50% of kittens receiving 0.02% monensin increased during toxoplasma infection, whereas all kittens on regular food lost weight. Eight uninfected, two months old just weaned kittens from 2 litters (750-1130 gm), were assigned to a diet of 0.02% monensin and to unmedicated ground Purina kitten chow, both supplemented with about 50 ml of milk/kitten/day for seven weeks. Kittens given monensin food gained an average of 197 gm (21%) and the unmedicated kittens an average of 214 gm (27%). There was greater variability in final weights of the kittens on medicated food (−37% [16 days], −20%, +62% in males, and +30% in a female) than of kittens on the unmedicated ground food −33% [28 days] in a male, and +15%, +21%, +48% in females). In both groups the smaller kittens ate less well, and the control kittens lost so much weight in the first two weeks that they were supplemented with unground kitten chow for three weeks till they ate better.

One kitten in the control group died with pneumonia and a pericardial hemorrhage at 16 days. One of the monensin-fed kittens died, immediately after bleeding at four weeks with pericardial tamponade.

Hematologic and blood chemistry values were obtained prior to, and after four and seven weeks of treatments. Starting with a blood urea nitrogen of 29±4.3 mg/dl, control values were 34±4.5 and 35.6±2.5 after four and seven weeks, compared to 44.0±6.4 and 44.3±1.5 in the monensin treated cats. There were no significant differences in the values of serum sodium, potassium, chloride, $CO_2$, glucose, creatinine, total protein, albumin, total bilirubin, alkaline phosphatase, glutamic oxalacetic transferase, cholesterol, uric acid, calcium and phosphorus between the monensin treated and control group, nor in the white blood count, red blood count, hemoglobin, hematocrit, index of red cell width or platelets. Histologic examination of the four kittens treated with monensin for four or seven weeks revealed no abnormalities in the brain, eye, thyroid, heart, lungs, aorta, liver, gallbladder, spleen, kidney, adrenals, skin, lymph nodes, small intestine, pancreas, skeletal muscle, ovary or bone marrow.

In order to find out whether cats had an aversion to monensin at any given drug level, a group of three kittens were offered different concentrations of monensin for eight days during a period of 15 days. The mean daily consumption in grams was: unmedicated, 7.8±2.8, 0.01%—3.5±1.9, 0.02%—21.5±4.6, and 0.03%—14.6±3.8. Thereafter, the same three kittens consumed the following quantities on seven days sampled during a period of 40 days; unmedicated 8.0±2.8, 0.02%—5.3±2.3, 0.03%—9.4±3.1, and 0.04%—5.0±2.2 grams.

TABLE 1

Effects of 100 and 200 mg/kg monensin given in cat food for eight days or longer on shedding of Toxoplasma oocysts, antibody development, and immunity to Toxoplasma challenge.

| Monensin in Food | | Kittens | | Reciprocal Antibody Titer | | Immune to Challenge |
|---|---|---|---|---|---|---|
| mg/kg | Days 0 = day of infection | No. | Shed | (28-62 Day) | Died | |
| 200 | −2 to 6-19 | 9 | 0 | <2-256 | 0 | 7/9[1] |
| 100 | −2 to 6-19 | 4 | 3 | 64-512 | 0 | 4/4 |
| None | (control) | 10 | 10 | <2-256 | 1[2] | 8/9 |

[1]Reciprocal antibody titers in those immune: <2, <4, 8, 16, 64, 256. Antibody titers in those not immune:<4, 2.
[2]Kitten weighed 740 when infected; floated feces showed 748, 114 and 37 oocysts per high power field on days 5, 6-7 and 8 when it died.

TABLE 2

Effects of 200 mg/kg of monensin given for various periods of time during the enteric cycle of Toxoplasma, after feeding bradyzoites.

| Kitten No. | Period of Drug Administration 0 = day of Infection | Oocyst Shedding Days After Infection | Intensity | Post Infection Antibody Titer | Immunity to Challenge In Relation to Infection | Post-Challenge Antibody Titer |
|---|---|---|---|---|---|---|
| 1 | −2 to 1+ | 10 | 1 | Died 14 Day | [b]Na | Na |
| 2 | −2 to 2 | 9 | 1 | 512 | Yes | 512 |
| 3 | −2 to 3 | 10–11 | 1 | 4000 | Yes | 2000 |
| [a]4 | −2 to 6 | — | 0 | 256 | Yes | 128 |
| [a]5 | −2 to 10 | — | 0 | <4 | Yes | 256 |
| 6 | 0 to 14 | — | 0 | 8 | Yes | 4 |
| 7 | 1 to 15 | — | 0 | 16 | Yes | 16 |
| 8 | 2 to 4 | 6–14 | 4 | 16 | Na | Na |
| 9 | 2 to 6 | 11–15 | 2 | 256 | Na | Na |
| 10 | 2 to 16 | — | 0 | 64 | Yes | 4 |
| 11 | 3 to 17 | 6–8 | 4 | 64 | Yes | 4 |
| 12 | 4 to 18 | 5–8 | 4 | 4 | Yes | <2 |
| 13 | 4 to 13 | 4–11 | 4 | 128 | Yes | 16 |
| 14 | 5 to 7 | 5–11 | 4 | Died 7 Day | Na | Na |
| [a]15–24 | None | 5–12 | mean 3.2 | | 8/9 | |

[a]Also listed in Table 1.
[b]Na = not applicable.

DISCUSSION

The foregoing results (Table 1) demonstrate effective levels (e.g., 0.02%) of monensin in cat food inhibited oocyst shedding in all of the nine cats infected with bradyzoites from chronically infected mice. Oocyst suppression was complete when treating from two days before infection to six days after infection, or from 2 to 16 days after infection (Table 2). Treatment for the first three days only prolonged the prepatent period and markedly diminished oocyst shedding. Starting treatment on the third day or later failed to be effective. From this it appears that treatment from two to four days after infection is most important. It appears that some drug effect might have been present on the sporozoites and stages A, B, and C, present at days 0–2, but that the essential effects were on stage D present on days two to four after infection (Dubey and Frenkel, "Cyst-induced toxoplasmosis in cats", *J. Protozool.* 19:155–177 (1972)). An effect on gametocytes is unlikely because treatment instituted on day three was followed by good oocyst production starting on day 6 after infection.

It is significant that in ten of twelve kittens immunity was found even though oocyst shedding had been initially suppressed by monensin. This compared with immunity in eight out of nine of the controls and in four out of four kittens treated with 0.01% monensin, all of which except one had shed oocysts.

It is known that cats that shed oocysts during their primary infection generally do not shed after reinfection. However, a drawback of using a natural infection for immunization is the contamination of the cat's environment with possibly millions of oocysts. On the other hand, attempts to employ for vaccination strains of Toxoplasma that have lost the capacity to form oocysts have been unsuccessful, making it seem that prior oocyst formation might be necessary for immunization against subsequent oocyst shedding. Therefore it was surprising to find that immunization can take place with the present invention even if part of the enteric cycle and oocyst production is suppressed. Somewhat similar observations were reported by Sheffield and Melton ("Effects of Development of *Toxoplasma gondii* in Cats", *Am.J.Trop.Med.Hyg.*, 25:379–383 (1976)) in three out of four cats treated intramuscularly with pyrimethamine and sulfadiazine and in two out of three cats being treated with 5 mg/kg of lasalocid orally (Sheffied and Melton, personal communication, 1976). However, the latter disclosure is deemed deficient in that oocyst shedding was only temporarily suspended using the lasalocid.

An antibody response of cats in the dye test was interpreted to indicate infection, although the lack of response cannot be interpreted with certainty. No antibody was found (1:2 final dilution) in spite of 3+ oocyst shedding in one control kitten (immune to challenge), and in three treated kittens that did not shed, two of which were immune to challenge. After the first challenge, 5 of 23 cats were seronegative; two as before, and three turned negative from prior titers of 4, 8, and 16. The rare failure of antibody development after oocyst shedding has been observed previously (Dubey and Frenkel, "Cyst-Induced Toxoplasmosis in Cats", *J. Protozool.* 19:155–177 (1972)), and was there associated with immunity; it appears to be more common after infections in prophylactically treated cats that had not shed oocysts. The seronegative kittens were not distinguished from those that reacted serologically, by weight, or prior Cystoisospora infection. Whether these cats actually sustained an infection of their internal organs, or were only stimulated antigencially from the enteroepithelial stages to develop immunity without circulating antibody was not clarified because all of the cats were challenged.

The safety of the effective drug dose was tested by giving 0.02% monensin for an extended period of time. The medicated food was well tolerated for seven weeks as indicated by the kittens' weight gain, which was similar to the controls, by similar hematologic and serum chemistry values, and by the absence of histopathic lesions. A minor decrease in urea clearance by the monensin treated kittens was of no apparent significance because of similar values, whether a kitten lost 20% of its body weight or gained 30% or 62% over seven weeks, and because of absence of dehydration, bleeding, heart failure, or histologic muscle lesions.

Unlike dogs, were males show a lesser tolerance than females, and where toxic myopathy has been reported, a male kitten showed the greatest weight gain, 62%, while on monensin food for seven weeks. The variability in weight gain was attributed to variable intake of ground food by the freshly weaned kittens with lowest body weight. The control kittens refused ground food initially, but accepted normal kitten chow as particulates or small "doughnuts" and gradually became adjusted to eating ground food; the kittens on medicated food accepted ground kitten chow more readily. The effective drug dose appears to be well accepted by cats. In the presence of unmedicated food and with discontinuous use, 0.03% was the preferred concentration in one test and 0.02% in the other.

The preferred drug, monensin, is a biologically active compound produced by a fermentation process and is identified as 2-[5-Ethyltetrahydro-5-[tetrahydro-3-methyl-5-[tetrahydro-6-hydroxy-6-(hydroxymethyl)-3,5-dimethyl-2H-pyran-2-yl]-2-furyl]-2-furyl]-9-hydroxy-$\beta$-methoxy-$\alpha,\gamma$,2,8-tetramethyl-1,6-dioxaspiro[4.5]decane-7-butyric acid. Salinomycin is characterized in a paper entitled "The Site of Action of the Anticoccidial Salinomycin (coxistac)", *J. Parasitol.*, Vol. 65, p. 137 (1979), and this paper is incorporated by reference herein.

We claim:

1. A method of preventing or minimizing shedding of Toxoplasma oocysts by a cat after Toxoplasma infection of such cat, comprising the steps of administering to the cat, prior to the onset of oocyst shedding, an effective amount of an agent selected from the group consisting of monensin and salinomycin, and continuing such administration for a period of time thereafter sufficient to maintain said prevention or minimization.

2. The method as set forth in claim 1, said administration commencing within 2 days from the time of ingestion by said cat of Toxoplasma-infected food, and continuing for a period of at least about two weeks thereafter.

3. The method as set forth in claim 1, said agent being admixed with and fed with the daily ration of said cat.

4. The method as set forth in claim 3, said agent being monensin, and being administered at a level of at least about 200 mg. per kg. of cat ration.

5. The method as set forth in claim 4, said level being from about 200 to 300 mg. per kg. of cat ration.

6. The method as set forth in claim 3, said agent being salinomycin, and being administered at a level of at least about 50 mg. per kg. of cat ration.

7. The method as set forth in claim 6, said level being from about 50 to 100 mg. per kg. of cat ration.

8. The method as set forth in claim 1, said agent being monensin and being administered at a level of from about 6 to 8 mg. per kg. per day of body weight of said cat during said period of time.

9. The method as set forth in claim 1, said agent being salinomycin and being administered at a level of from about 2 to 3 mg. per kg. per day of body weight of said cat during said period of time.

* * * * *